United States Patent [19]

Clémence et al.

[11] Patent Number: 5,126,353
[45] Date of Patent: * Jun. 30, 1992

[54] COMPOSITIONS AND METHOD OF TREATING ARRYTHMIA WITH TETRAHYDROPYRIDINES

[75] Inventors: François Clémence; Daniel Frechet; Michel Fortin, all of Paris, France

[73] Assignee: Roussel Uclaf, Paris, France

[*] Notice: The portion of the term of this patent subsequent to May 22, 2007 has been disclaimed.

[21] Appl. No.: 489,374

[22] Filed: Mar. 6, 1990

Related U.S. Application Data

[62] Division of Ser. No. 214,673, Jul. 11, 1988, Pat. No. 4,927,832.

[30] Foreign Application Priority Data

Jul. 3, 1987 [FR] France .................. 87 09449

[51] Int. Cl.[5] ............... H61K 31/505; H61K 31/435; H61K 31/47
[52] U.S. Cl. .................... 514/299; 514/256; 514/314
[58] Field of Search ............ 514/256, 299, 314

[56] References Cited

U.S. PATENT DOCUMENTS 4,927,832 5/1990 Clemence et al. ............ 514/299

*Primary Examiner*—Robert T. Bond
*Assistant Examiner*—F. Bernhardt
*Attorney, Agent, or Firm*—Bierman and Muserlian

[57] ABSTRACT

Novel enantiomeric and diasteroisomeric forms of tetrahydropyridines of the formula

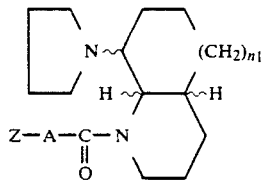

wherein $n_1$ is 0 or 2, A is selected from the group consisting of $-(CH_2)_{n2}-$ and alkylene substituted with alkyl having a total of 2 to 8 carbon atoms and $n_2$ is 0 to 5, Z is selected from the group consisting of phenyl, naphthyl, indenyl, heteromonocycle of 5 to 6 ring members and heterobicycle, each optionally substituted with at least one substituent and their non-toxic, pharmaceutically acceptable acid addition salts and quarternary ammonium salts having central analgesic properties as well as diuretic, anti-arrhythmic, anti-cerebral-ischemia and hypotensive properties.

6 Claims, No Drawings

COMPOSITIONS AND METHOD OF TREATING ARRYTHMIA WITH TETRAHYDROPYRIDINES

PRIOR APPLICATION

This application is a division of U.S. patent application Ser. No. 214,673 filed Jul. 11, 1988, now U.S. Pat. No. 4,927,832.

STATE OF THE ART

Related pyridines are described in U.S. Pat. Nos. 4,337,341 and No. 4,677,122 and U.S. patent application Ser. No. 002,778 filed Jan. 13, 1987.

OBJECTS OF THE INVENTION

It is an object of the invention to provide the novel compounds of formula I and their salts and a process and novel intermediates for their preparation.

It is another object of the invention to provide novel analgesic compositions and a novel method of relieving pain and of treating arrythmia in warm-blooded animals.

These and other objects and advantages of the invention will become obvious from the following detailed description.

THE INVENTION

The novel compounds of the invention are selected from the group consisting of all enantiomeric and diastereoisomeric forms of tetrahydropyridines of the formula

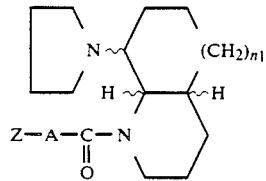

wherein $n_1$ is 0 or 2, A is selected from the group consisting of —$(CH_2)_{n2}$— and alkylene substituted with alkyl having a total of 2 to 8 carbon atoms and $n_2$ is 0 to 5, Z is selected from the group consisting of phenyl, naphthyl, indenyl, heteromonocycle of 5 to 6 ring members and heterobicycle, each optionally substituted with at least one substituent and their non-toxic, pharmaceutically acceptable acid addition salts and quaternary ammonium salts.

When A is —$(CH_2)_{n2}$—, $n_2$ is preferably 0 or 1 and when A is an alkyl substituted alkylene, the alkyl is preferably methyl or ethyl which means A may be 1,1-ethanediyl, 1-methyl-1,2-ethanediyl, 1-methyl- or 2-methyl-1,3-propanediyl, or a 1-ethyl-1,2-ethanediyl radical.

When Z is heteromonocyclic of 5 to 6 links, it is preferably thiazolyl, pyridinyl, oxazolyl, isoxazolyl, imidazolyl, thienyl, furyl or pyrimidinyl. When Z is heterobicyclic, it is preferably indolyl, quinolyl, benzofuranyl, benzo[b]thienyl, benzimidazolyl, benzoxazolyl or benzothiazolyl.

When Z is phenyl, naphthyl, indenyl or substituted heterocyclic, the substituents are selected from the group consisting of alkyl of 1 to 5 carbon atoms, alkoxy of 1 to 5 carbon atoms, halogen, hydroxyl, trifluoromethyl, nitro, amino, monoalkyl- or dialkylamino with alkyls of 1 to 5 carbon atoms.

Among the alkyl, alkoxy or halogen, it is preferably methyl, ethyl, linear or branched propyl or butyl, methoxy, ethoxy, linear or branched propoxy or butoxy, fluoro, chloro, bromo or iodo. In the monoalkyl- and dialkylamino, the alkyls are preferably methyl or ethyl.

Furthermore, the compounds of formula I can exist in the form of four racemates, or pairs of enantiomers. The enantiomers of each pair can be separated by standard processes. The invention therefore covers all the enantiomeric and diasteroisomeric forms of the compounds of formula I.

Examples of acid addition salts with mineral or organic acids are for example, the salts formed with the following acids: hydrochloric acid, hydrobromic acid, nitric acid, sulfuric acid, phosphoric acid, acetic acid, propionic acid, formic acid, benzoic acid, maleic acid, fumaric acid, succinic acid, tartaric acid, citric acid, oxalic acid, glyoxylic acid, aspartic acid, alkanesulfonic acids such as methane sulfonic acid and arylsulfonic acids such as benzene sulfonic acid.

The invention is also concerned with compounds of formula I in the form of quaternary ammonium salts. By quaternary ammonium salts, there is meant compounds of formula I quaternized by products of the type R-Y, R being alkyl of 1 to 4 carbon atoms such as methyl, ethyl, n-propyl or isopropyl, and Y is halide anion, for example chloride, bromide or iodide.

In particular, the invention is concerned with compounds with the formula I in which A is $(CH_2)_{n2}$— where $n_2$ is 0 or 1 or 1,1-ethanediyl as well as their addition salts with acids and their quaternary ammonium salts. More particularly, the invention also includes compounds of formula I in which Z is phenyl, naphthyl, pyridinyl, thienyl, indolyl, or benzo[b]thienyl unsubstituted or substituted by at least one substituent as well as their addition salts with acids and their quaternary ammonium salts.

More particularly, the invention is concerned with compounds of formula I in which Z is phenyl substituted by at least one substituent chosen from the group constituted by halogen, trifluoromethyl or nitro, or Z is naphthyl or benzo[b]thienyl as well as their addition salts with acids and their quaternary ammonium salts. Specific preferred compounds are: [4a RS (4a-α, 7aβ-)] (±) 1-[(3,4-dichlorophenyl)-acetyl]-octahydro-7-(1-pyrrolidinyl)-1H-1-pyrindine, [4a RS (4aα-, 7aα-)] (±) 1-[(3,4-dichlorophenyl)-acetyl]-octahydro-7-(1-pyrrolidinyl)-1H-1-pyrindine(isomer cis I) and their acid addition salts and their quaternary ammonium salts.

"Isomer cis I" represents the product presenting the weakest Rf.

The novel process of the invention for the preparation of compounds of formula I comprises reacting a compound of the formula

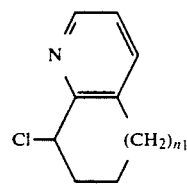

wherein $n_1$ is 0 or 2 with pyrrolidine to obtain a compound of the formula

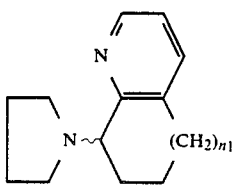

reducing the latter to obtain a compound of the formula

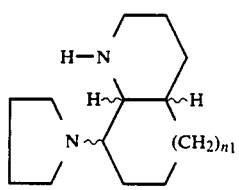

which, if desired, the different isomers are separated and condensing the latter with a compound of the formula

or a functional derivative of this compound wherein A and Z have the above definitions to obtain a compound of formula I in all its possible enantiomeric and diastereoisomeric forms, which is treated if desired with a mineral or organic acid to obtain a salt or with an alkyl halide to obtain a quaternary ammonium salt.

In a preferred mode of the process, the condensation of the product of formula II with the pyrrolidine in an aqueous medium is carried out at a temperature between 20° C. and 120° C. The reduction of the compound of formula III is a catalytic hydrogenation and the catalyst preferably used is platinium oxide. This reduction is carried out in the presence of an acid such as hydrochloric acid. The hydrogenation of the products of formula III leads to the different isomers at the junction of the cis or trans ring, each of the two cis or trans isomers being able to carry the pyrrolidinyl in an α or β orientation. The activation of the carboxyl of the compound of formula V to realize the condensation with the compound of formula IV is carried out in the presence of carbonyldiimidazole or dicyclohexylcarbodiimide. The acid of formula IV can also be activated in the form of an acid chloride or of a mixed anhydride. These different isomers are separated by chromatography.

The compounds with the formula (I) as defined above as well as their addition salts with acids show useful pharmacological properties. They show in particular a strong affinity for the opiate receptors and in particular for the K receptors and are endowed with central analgesic properties.

They are also endowed with diuretic properties and anti-arrythmic, anti-cerebral, ischaemic and hypotensive properties.

The novel central analgesic compositions of the invention are comprised of an analgesically effective amount of at least one compound of formula I and its non-toxic, pharmaceutically acceptable acid addition salts and quaternary ammonium salts and an inert pharmaceutical carrier or excipient. The compositions may be in the form of tablets, dragees, capsules, granules, suppositories, ointment, creams, gels, aerosol preparations and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents and preservatives.

The analgesic compositions are useful for the relief of pain, whatever its origin, for example a pain of muscular, articular or nervous nature. They can also be used in the treatment of dental pains, migrains, and herpes zoster, in the treatment of intense pains, in particular those resistant to peripheral analgesics, for example, in the course of neoplasic processes, in the treatment of pancreatitis, nephretic or biliar colics, in the treatment of post-operative and post-traumatic pains.

The novel anti-arrythmic compositions are comprised of an anti-arrythmically effective amount of at least one compound of formula I and its non-toxic pharmaceutically acceptable acid addition salts and quaternary ammonium salts and an inert pharmaceutical carrier or excipient.

The compositions may also be used in the treatment of oedematous syndromes, of cardiac insufficiency, of certain obesities, of cirrhoses, in the treatment of severe and refractary oedemas, in particular those from congestive cardiac insufficiency and in the long term treatment of arterial hypertension. The compositions may be in the form of tablets, dragees, capsules, granules, suppositories, ointment, creams, gels, aerosol preparations and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents and preservatives.

Particularly preferred compositions of the invention contain as the active compounds a member of the group consisting of [4a RS (4a-α, 7aβ-)] (±) 1-[(3,4-dichlorophenyl)-acetyl]-octahydro-7-(1-pyrrolidinyl)-1H-1-pyrindine, [4a RS (4aα-, 7aα-)] (±) 1-[(3,4-dichlorophenyl)-acetyl]-octahydro-7-(1-pyrrolidinyl]-1H-1-pyrindine(isomer cis I) and their acid addition salts and their quaternary ammonium salts.

The novel method of the invention for relieving pain in warm-blooded animals comprises administering to warm-blooded animals an analgesically effective amount of at least one compound of formula I or its non-toxic, pharmaceutically acceptable acid addition salts or quaternary ammonium salts. The compounds may be administered orally, rectally, parenterally or topically to the skin or mucous. The daily dose will vary depending on the condition treated, the specific compound and the method of administration.

For example, for analgesic activity the usual daily oral dose is 0.25 to 5.35 mg/kg and the usual parenteral dose is 0.06 to 1.35 mg/kg daily.

The novel method of treating arrythmia in warm blooded animals including humans, comprises administering to warm-blooded animals a antiarythmically effective amount of at least one compound of formula I and its non-toxic, pharmaceutically acceptable acid addition salts and quaternary ammonium salts. The compounds may be administered preferably orally, rectally or parenterally and the usual daily dose is 0.5 to 13 mg/kg depending on the condition treated, the specific compound and method of administration. For example, the daily oral dose for the treatment of ventricular, supraventricular and junctional arrythmias is 3 to 12 mg/kg.

The novel method of treating oedematous syndromes, cardiac insufficiency, certain obesities, cirrhoses, severe and refractory oedemas and arterial hypertension in warm blooded animals including humans, comprises administering to warm-blooded animals an effective amount of at least one compound of formula I and its non-toxic, pharmaceutically acceptable acid addition salts and quaternary ammonium salts. The compound may be administered orally rectally or parenterally and the usual daily dose is 0.8 to 1.35 mg/kg depending on the condition treated, the specific compound and method of administration.

The starting compounds of formula II are prepared by chlorinating the corresponding hydroxy compounds which are described in J. Chem. Soc. Perkin Trans(1) 1973 (9) 968 to 972 and in J. Am. Chem. Soc. 80, 6254 (1958).

The novel intermediate compounds of the invention are the compounds of formulae II, III, and IV.

In the following examples there are described several preferred embodiments to illustrate the invention. However, it is to be understood that the invention is not intended to be limited to the specific embodiments.

EXAMPLE 1

[4aRS (4a-α, 7a-α)](±)1-[(3,4-dichlorophenyl)-acetyl]-octahydro-7-(1-pyrrolidinyl)-1H-1-pyrindine hydrochloride (isomer cis I)

STEP A: Hydrochloride of 7-chloro-6,7-dihydro-5H-1-pyrindine 10 g of 7-hydroxy-6,7-dihydro-5H-1-pyrindine dissolved in 100 ml of methylene chloride cooled to 0° C. were admixed with 20 ml of thionyl chloride and after stirring for 30 minutes at 0° C., 250 ml of ether were added with further stirring for 30 minutes at 0° C. After separating, washing with ether and drying under reduced pressure at 80° C., 13.60 g of product were obtained which was dissolved hot in 400 ml of methylene chloride, treated with active charcoal, filtered, and concentrated to about 100 ml. After cooling to ambient temperature, 200 ml of ether were added, and crystallization was allowed for 2 hours at ambient temperature, followed by separating and washing with ether to obtain 10.81 g of the expected product melting at 130° to 135° C.

STEP B: 7-(1-pyrrolidinyl)-6,7-dihydro-5H-1-pyrindine 5 g of 7-chloro-6,7-dihydro-5H-1-pyrindine hydrochloride were dissolved in 10 ml of water and 8.8 ml of pyrrolidine were added, followed by stirring for two-and-a-half hours at ambient temperature. Extraction was done with methylene chloride and the extracts were washed with water, dried and concentrated to dryness under reduced pressure. The residue was taken up in ethyl acetate, treated with active charcoal, filtered and taken to dryness under reduced pressure. The residue was chromatographed on silica and eluted with a mixture of ethyl acetate and triethylamine (95-5) to obtain 4.71 g of the expected product.

| NMR Spectrum (CDCl$_3$), ppm | | | |
|---|---|---|---|
| 8.41 | (d, J=5Hz) | H$_2$ | pyrindine |
| 7.06 | (dd, J=5 and 5Hz) | H$_3$ | pyrindine |
| 7.90 | (d, J=8Hz) | H$_4$ | pyrindine |
| 2.11 to 3.06 | | H$_5$, H$_6$ | pyrindine |
| 4.06 | (dd, J=5.5 and 8Hz) | H$_7$ | pyrindine |

STEP C: cis and trans isomers of (±) octahydro-7-(1-pyrrolidinyl)-1H-1-pyrindine 6.4 g of the product of Step B in 64 ml of methanol and 6.4 ml of concentrated hydrochloric acid were hydrogenated in the presence of platinum oxide for 5 hours under 1700 mbars and then filtered. The solvent was evaporated to dryness at 40° C. maximum under reduced pressure. The residue was taken up in 20 ml of water, alkalized with about 10 ml of a 32% solution of sodium hydroxide, extracted with methylene chloride, washed with water, dried, and taken to dryness under reduced pressure. The residue was chromatographed on silica and eluted with a mixture of ethyl acetate, methanol and triethylamine (80-15-5) to obtain:
2.2 g of isomer (cis II) rf 0.35
0.80 g of isomer (trans I) rf 0.20
0.15 g of isomer (cis I) rf 0.15

| NMR Spectrum (CDCl$_3$), ppm: | |
|---|---|
| Isomer cis I | |
| H$_{7a}$ | 3.11(dd, J=2 and 5Hz) |
| | (JH$_7$, H$_{7a}$=2.Hz and |
| | JH$_{4a}$, H$_{7a}$=5Hz) |
| CH$_2$ at 2 | 2.93(dt)H equ. |
| | 2.60(ddd)H ax |
| pyrrolidine | 2.54(m)H at alpha of N |
| | 1.77(m)H at beta of N |
| H$_7$ | 2.37(ddd, J=2-5-7Hz) |
| H$_{4a}$ and 1H of the CH$_2$ at H$_6$ | 2.01(m) |
| the other protons | 1.3 to 1.8 ppm |
| Isomer cis II | |
| CH$_2$ at 2 | 3.01(dt)H equ. |
| | ~2.45H ax |
| H$_{7a}$ | 2.90(dt, J=3.5Hz) |
| H$_7$ | 2.29(dt, J=3.5-9 and 9Hz) |
| | (J$_{H7}$, H$_{7a}$=3.5Hz) |
| pyrrolidine | ~2.46(m)H at alpha of N |
| | ~1.73(m)H at beta of N |
| H$_{4a}$ | ~1.99(m) |
| the other protons | 1.3 to 2.0 |
| Isomer trans I: | |
| CH$_2$ at 2 | 3.16(dm)H eq. |
| | 2.59 masked H ax. |
| H$_7$ | 3.03(dt, J~3-7 and 7Hz) |
| pyrrolidine | 2.70 and 2.59H at alpha of N |
| | ~1.70H at beta of N |
| H$_{7a}$ | 2.23(dd, J=11 and 7Hz) |
| the other protons | 0.9 to 2.1 |

STEP D: [4aRS (4a-α, 7a-α)] (±) 1-[(3,4-dichlorophenyl)acetyl]-octahydro-7-(1-pyrrolidinyl)-1H-1-pyrindine hydrochloride (isomer cis I)

1.43 g of dichlorophenyl-acetic acid were dissolved in 9.7 ml of tetrahydrofuran and 1.14 g of carbonyl diimidazole were added with stirring for 1 hour at ambient temperature. A solution of 0.972 g of isomer cis I of Step C dissolved in 9.7 ml of tetrahydrofuran was added with stirring for 5 hours at ambient temperature. The mixture was taken to dryness under reduced pressure and by heating to 40° C. After extracting the residue with ether, the organic phase was washed with a solution of sodium bicarbonate, then with water, dried and taken to dryness. The residue was chromatographed over silica and eluted with a mixture of ethyl acetate, methanol and triethylamine (80-15-5) to obtain 1.66 g of the expected product in the form of a base.

1.6 g of the latter were dissolved in 5 ml of ethyl acetate and an excess of a solution of hydrochloric acid in ethyl acetate was added. After allowing the mixture to crystallize, the crystals were separated to obtain 1.36 g of the expected hydrochloride melting at 228° C. after recrystallization from ethyl acetate.

| NMR Spectrum (CDCl$_3$), ppm | |
|---|---|
| —CH—N—C— <br> ‖ <br> O | 4.98(d, d J=6.5 and 9Hz) |
| C—CH$_2$-ϕ, CH$_2$N—C and H's at <br> ‖              ‖    alpha of N <br> O              O | 2.6 to 4.7(9H). |
| aromatic | 7.2 to 7.7 |
| H mobile | 11.7 and 12.9 |
| the other protons | 1.1 to 2.3 |

EXAMPLE 2

[4aRS (4a-α, 7aα)](±)-1-[(3,4-dichlorophenyl)acetyl]octahydro-7-(1-pyrrolidinyl)-1H-1-pyrindine hydrochloride (isomer cis II)

Using the procedure of Step D of Example 1, 0.97 g of isomer cis II of Step C of Example 1 were reacted and the residue was chromatographed on silica. Elution with a mixture of methyhlene chloride and methanol (9-1) yielded 1.37 g of free base which was converted into its hydrochloride, then recrystallized from ethanol to obtain 410 mg of the expected hydrochloride melting at 135° C., then 181° C.

| NMR Spectrum (CDCl$_3$), ppm: | |
|---|---|
| 1H of CH$_2$—CH—N | 2.43(m) |
| CH$_2$N—C <br> ‖ <br> O | 2.76(m) |
| CH$_2$N$^{\oplus}$ | 2.92(m) <br> 3.57 to 3.97 |
| O <br> ‖ <br> O—CH$_2$—C | { 3.75(d, J=15Hz) <br>   3.94(d, J=15Hz) |
| NCH—CH | (5.10)(t, J=8) |
| aromatics { H$_5$ <br>          H$_3$ and H$_6$ | 7.13(dd) <br> 7.40 |
| Other protons | 1.35 to 2.35 |

EXAMPLE 3

[4aRS (4aα, 7aβ)](±) 1-[(3,4-dichlorophenyl)acetyl]octahydro-7-(1-pyrrolidinyl)-1H-1-pyrindine hydrochloride (isomer trans I).

Using the procedure of Step D of Example 1, 0.75 g of isomer trans I of Step C of Example 1 were reacted and the residue was chromatographed on silica. Elution with a mixture of ethyl acetate, methanol and triethylamine (90-5-5) yielded 1.19 g of free base from which the hydrochloride was prepared and purified by dissolving in 5 ml of methylene chloride and treating with active charcoal. 10 ml of ether were added for crystallizing to obtain 370 mg of the expected hydrochloride melting at 202° C.

| NMR Spectrum (CDCl$_3$) ppm: | | |
|---|---|---|
| CH$_2$ at 2 | | } 4.07(td, J=13.5–13.5–4.5Hz) <br> ~3.65(masked) |
| H$_7$ | | ~3.87 |
| CO—CH$_2$-O | | 3.69 |
| H$_{7a}$ axial | | 3.37(dd, J=6 and 14Hz) |
| H$_{4a}$ axial | | 3.12(m) |
| CH$_2$N-pyrrolidine | | } 3.87 1H <br> 3.50 1H <br> 2.75 2H |
| H$_5$ | | {7.67(d,d) |
| H$_3$ | aromatics | } 7.35(d) |
| H$_6$ | | 7.41(d) |
| H mobile | | 11.80(S) |
| other protons | | 1.00 to 2.30 |

EXAMPLE 4

[4a-α, 9-β, 9a-α] (±) decahydro-1-([3,4-dichlorophenyl)acetyl]-9-(1-pyrrolidinyl)-1H-cyclohepta[b]pyridine hydrochloride

STEP A:

9-(1-pyrrolidinyl)-6,7,8,9-tetrahydro-5H-cyclohepta[b]pyridine 5 g of 9-chloro-6,7,8,9-tetrahydro-5H-cyclohepta[b]pyridine hydrochloride were dissolved in 12.5 ml of water and 8 ml of pyrrolidine were added. The mixture was refluxed with vigorous stirring for 5 hours and the excess pyrrolidine was evaporated off under reduced pressure. 25 ml of a saturated solution of sodium bicarbonate and then 50 ml of water were added followed by extraction with methylene chloride. The combined organic phases were washed with water, dried and concentrated to dryness under reduced pressure. The residue was chromatographed on silica and eluted with a mixture of methylene chloride and methanol (9-1) to obtain 2.25 g of the expected product with an Rf=0.20. 2.25 g of the product were crystallized from petroleum ether (b.p. 40°-70° C.) to obtain 2 g of the expected product melting about 62° C.

hydrochloride of 9-chloro-6,7,8,9-tetrahydro-5H-cyclohepta[b]pyridine 26 g of 9-hydroxy-6,7,8,9-tetrahydro-5H-cyclohepta[b]pyridine hydrochloride in 520 ml of methylene chloride and 130 ml of thionyl chloride were refluxed for 1 hour and after evaporating almost to dryness under reduced pressure at about 45° C., 26 ml of ethyl acetate were added. Crystallization was initiated and the crystals were separated to obtain 24 g of product which was dissolved in 40 ml of methanol. 100 ml of methylethyl ketone were added and the mixture was concentrated to 80 ml, filtered, then concentrated to 30 ml. Crystallization was initiated to obtain 20.4 g of the expected product melting at about 150° C.

STEP B: [4a-α, 9-β, 9a-α](±) decahydro-9-(1-pyrrolidinyl)-1H-cyclohepta[b]pyridine Using the procedure of Step D of Example 1, hydrogenating for 3 hours 4.2 g of the product obtained above (m.p. about 62° C.) yielded 4 g of the expected product melting at about 30°-35° C.

STEP C: [4a-α, 9-β, 9a-α](±) decahydro-1-[3,4-dichlorophenyl)-acetyl]-9-(1-pyrrolidinyl)-1H-cyclohepta[b]pyridine hydrochloride Using the procedure of Step D of Example 1, 2.22 g of the product of Step B were reacted and chromatographing the residue on silica, eluting with a mixture of methylene chloride and methanol (9-1) yielded 1.75 g of the expected product in the form of a base which was dissolved in 10 ml of ethyl acetate. An excess of a solution of hydrochloric acid in ethyl acetate was added, and crystallization was allowed to obtain 1.65 g of the expected hydrochloride melting at about 190° C. The latter was taken up hot in 20 ml of ethanol, filtered, returned to 20° C. and 30 ml of ether were added. Crystallization was initiated and allowed for 16 hours, then, after separating, 1.2 g of the expected product melting at about 110° C., then about 190° C. were obtained.

| UV Spectrum (Ethanol): | | | |
|---|---|---|---|
| Inflexion | 220 nm | $E_1^1 = 303$ | $\epsilon = 13{,}500$ |
| Inflexion | 222 nm | $E_1^1 = 274$ | |
| Inflexion | 227 nm | $E_1^1 = 218$ | |
| Inflexion | 260 nm | $E_1^1 = 4$ | |
| Maximum | 268 nm | $E_1^1 = 6$ | |
| Maximum | 272 nm | $E_1^1 = 8.5$ | $\epsilon = 400$ |
| Maximum | 281 nm | $E_1^1 = 8$ | |

EXAMPLE 5

[4a-α(9-α, 9a-α)] (±) decahydro-(1-[3,4-dichlorophenyl) acetyl]-9(1-pyridinyl)-1H-cyclohepta[b]pyridine hydrochloride Using the procedure of Step C of Example 4, [4a-α, 9-α, 9a-α] (±) decahydro-9-(1-pyrrolidinyl)-1H-cyclohepta[b]-pyridine (m.p. +65° C.), itself obtained by chromatography after the reduction of Step B, was reacted to obtain the expected product melting at 150° C., then 250° C.

EXAMPLE 6

Tablets were prepared containing 200 mg of the product of Example 1 and sufficient excipient of lactose, talc, starch and magnesium stearate for a final weight of 800 mg.

EXAMPLE 7

An injectable solution (intra-muscular route) was prepared containing 50 mg of the product of Example 1 and sterile solvent for a final solution of 5 ml.

PHARMACOLOGICAL STUDY

1) Liaison to the K opiated receptor in vitro

Membrane residues preserved at −30° C. (possibly up to about 30 days) and prepared from the brains of guinea pigs were used. The residues were suspended in Tris pH 7.7 buffer and fractions of 2 ml were distributed in hemolysis tubes, $9^3H$ ethylketocyclazocine 1 nM and the product under study were added. The product was first tested at $5 \times 10^{-6}M$ (in triplicate). When the product tested displaced the radioactivity bound specifically to the receptor by more than 50%, it was again tested according to a range of 7 doses to determine the dose which inhibits the radioactivity bound specifically to the receptor by 50%. In this way, the 50% inhibiting concentration was determined.

The non-specific liaison was determined by adding the product known as U-50488 H (Lahti et al. 1982, Life Sci. 31, 2257) at $10^{-5}M$ in triplicate. After incubating at 25° C. for 40 minutes, returning to the water-bath at 0° C. for 5 minutes, filtering under vacuum, and rinsing with Tris pH 7.7 buffer, the radioactivity was counted in the presence of scintillating Trition. The result was expressed directly as the 50% inhibiting concentration ($IC_{50}$), (that is to say, as the concentration of the product studied, expressed in nM, necessary to displace 50% of the specific radioactivity fixed on the receptor studied. The $IC_{50}$ found was 4 nanomoles for the product of Example 1 and 9 nanomoles for the product of Example 3.

2). Anti-arrhythmic activity in the rat

Male rats weighing 300–350 g, anesthetized intraperitoneally with 1.20 g/kg of urethane, were tracheotomised and submitted to artificial respiration (40–50 insufflations of 3 ml/minute). Needles were implanted sub-cutaneously to record the electrocardiogram of the rats on the DII derivation signal and the products under test were administered intravenously. Five minutes after administering the product, the jugular vein of the rats was perfused with 10 μg/mn from 0.2 ml of an aconitine solution and the time of appearance of disturbances of the cardiac rhythm was noted. The results were expressed as percentage of extension of the time of appearance of the cardiac rhythm disturbances as compared with controls and as a function of the dose of the product tested. The results appearing on the following table show that certain of the products of the present application are endowed with good anti-arrhytmic properties.

| Product of Example | Dose mg/kg | Percentage of extension of the time |
|---|---|---|
| 1 | 2.5 | +35% |
|   | 1   | +26% |
| 4 | 2.5 | +65% |
|   | 1   | +37% |

3). Measurement of diuretic activity

Male rats of Sprague Dawley strain weighing 180–200 g were deprived of food for 17 hours before the test, while receiving water ad libitum. Groups of 8 animals were set up for each dose tested and the rats received the product under test or its vehicle orally. The urine volume was measured every hour for the 5 hours following the administration of the product. After this period, the urines were collected and the activity of the product was expressed as a percentage of variation calculated on the urinary volume corresponding to the period $t_{0h}$–$t_{5h}$. The following are the results obtained:

| Product | Dose | Percentage of variation of the urine volume |
|---|---|---|
| Example 1 | 5 mg/kg | +85% |
| Example 3 | 5 mg/kg | +57% |

4). Analgesic activity

This test was based on the observation of Koster et al (Fed. Proc. 1959, 1B, 412) that the intraperitoneal injection of acetic acid causes repeated movements of stretching and twisting in rodents which can be considered as manifestations of a diffuse abdominal pain because they are attenuated by analgesics. The acetic acid was injected at a dose of to male mice of average weight of 100 g. The product under study was administered orally 30 minutes before the injection of the acetic acid to groups of 10 animals, each trial including a control group which receives the vehicle. Five minutes after the injection of the irritant, the stretchings and twistings were counted for each animal for a period of 15 minutes. The analgesic effect of each dose of product studied was expressed as a percentage of protection in relation to the average number of movements observed in the controls receiving acetic acid alone. The $DA_{50}$ or dose necessary to reduce the number of stretchings by 50% was calculated according to the method of least squares. The $DA_{50}$ values obtained with the products of Example 1 and 3 were respectively 2.5 and 5 mg/kg.

Various modifications of the compounds and method of the invention may be made without departing from the spirit or scope thereof and it is to be understood that the invention is intended to be limited only as defined in the appended claims.

What we claim is:

1. A method of treating arrythmia in warm-blooded animals comprising administering to warm-blooded animals an anti-arrythmically effective amount of at least one compound selected from the group consisting of all enantiomeric and diasteroisomeric forms of tetrahydropyridines of the formula

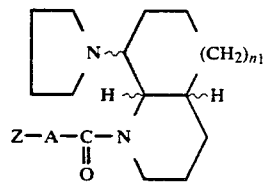

wherein $n_1$ is 0 or 2, A is selected from the group consisting of —$(CH_2)_{n2}$— and alkylene substituted with alkyl having a total of 2 to 8 carbon atoms and $n_2$ is 0 to 5, Z is selected from the group consisting of phenyl, naphthyl, indenyl, thiazolyl, pyridinyl, oxazolyl, isoxazolyl, imidazolyl, thienyl, furyl, pyrimidinyl, indolyl, quinolyl, benzofuranyl, benzothienyl, benzimidazolyl, benzoxazolyl and benzothiazolyl, each optionally substituted with at least one substituent selected from the group consisting of alkyl of 1 to 5 carbon atoms, alkoxy of 1 to 5 carbon atoms, halogen, hydroxyl, trifluoromethyl, nitro, amino and monoalkyl- or dialkylamino with alkyls of 1 to 5 carbon atoms and their non-toxic, pharmaceutically acceptable acid addition salts and quaternary ammonium salts.

2. A method of claim 1 wherein A is —$(CH_2)_{n2}$— and $n_2$ is 0 or 1 or 1,1-ethanediyl.

3. A method of claim 1 wherein Z is selected from the group consisting of phenyl, naphthyl, pyridinyl, thienyl, indolyl and benzothienyl, all unsubstituted or substituted.

4. A method of claim 1 wherein Z is phenyl or phenyl substituted with at least one member of the group consisting of halogen, —$CF_3$ and —$NO_2$.

5. A method of claim 1 wherein Z is naphthyl or benzothienyl.

6. A method of claim 1 wherein the compound is selected from the group consisting of [4a RS)4a-α 7a-β)(+)1-[(3,4-dichlorophenyl)-acetyl]-octahydro-7-(1-pyrrolidine)-1H-pyrindine, [4a RS (4a-α 7a-α)(+) 1-[(3,4-dichlorophenyl)-acetyl]-octahydro-7-(1-pyrrolidinyl)-1H-1-pyrindine (isomer cis I).

* * * * *